United States Patent [19]

Goodall et al.

[11] Patent Number: 5,012,101
[45] Date of Patent: Apr. 30, 1991

[54] OPTICAL APPARATUS AND METHOD

[75] Inventors: David M. Goodall, Huntington; David K. Lloyd, Bath, both of England

[73] Assignee: National Research Development Corporation, London, England

[21] Appl. No.: 440,425

[22] Filed: Nov. 21, 1989

Related U.S. Application Data

[63] Continuation of Ser. No. 216,626, filed as PCTGB87/00752 on Oct. 23, 1987, published as WO88/03266 on May 5, 1988, now abandoned.

[30] Foreign Application Priority Data

Oct. 24, 1986 [GB] United Kingdom ............... 8625530

[51] Int. Cl.[5] .............................................. G01N 21/21
[52] U.S. Cl. .................................. 250/343; 250/373; 356/366
[58] Field of Search ................. 250/343, 373; 356/368, 356/367, 366, 364; 350/407, 413, 96.29

[56] References Cited

U.S. PATENT DOCUMENTS

| | | | |
|---|---|---|---|
| 4,467,204 | 8/1984 | Kysilka et al. | 250/343 |
| 4,498,774 | 2/1985 | Yeung et al. | 356/368 |
| 4,622,465 | 11/1986 | Harig et al. | 250/373 |

FOREIGN PATENT DOCUMENTS

| | | | |
|---|---|---|---|
| 0087535 | 9/1983 | European Pat. Off. | |
| 60-184225 | 9/1985 | Japan | 350/407 |
| 8602162 | 4/1986 | World Int. Prop. O. | |
| 8803266 | 5/1988 | World Int. Prop. O. | 356/368 |

OTHER PUBLICATIONS

P. Akahavan Leiabady, J. D. C. Jones and D. A. Jackson, "Combined Interferometric-Polarimetric Fibre Optic Sensor Capable of Remote Operation", *Optics Communications*, vol. 57, No. 2 (Feb. 15, 1986), pp. 77-80, Copyright ©, 1986 Elsevier Science Publishers B.V.

*Primary Examiner*—Constantine Hannaher
*Attorney, Agent, or Firm*—Cushman, Darby & Cushman

[57] ABSTRACT

High pressure liquid chromatography apparatus for use in the analysis of optically-active materials comprises a semiconductor laser diode radiation source 10, a test sample holder 13 through which radiation from the radiation source passes to a detector 16. A polariser 11 and analyser 15 cooperate with a modulator 12 which modulates the rotation of the polarisation of radiation from the laser.

7 Claims, 8 Drawing Sheets a. Dilute solution                    0.05% Gum
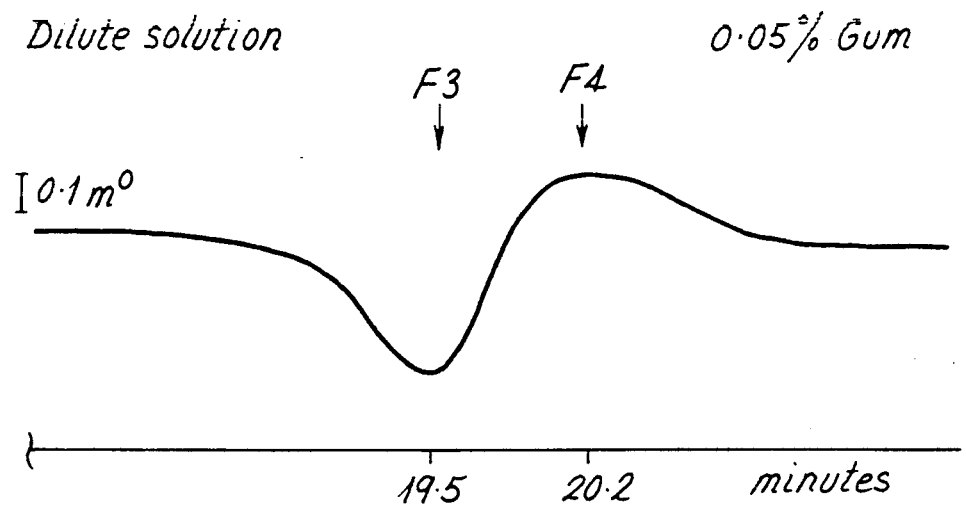
b. More concentrated solution         0.05% Gum
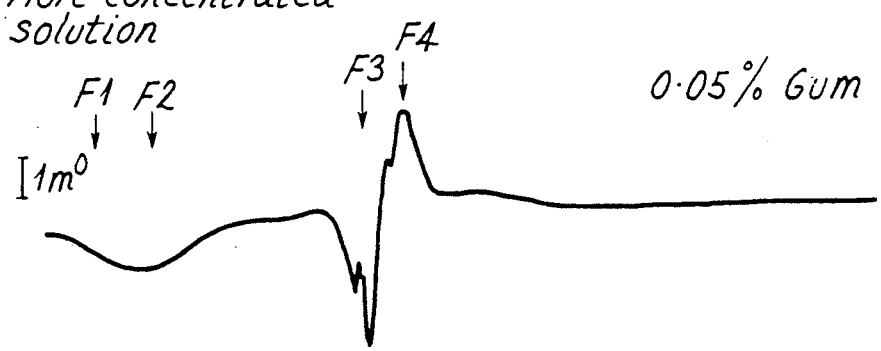
c. Carrier signal amplitude for trace in (b) on same timescale
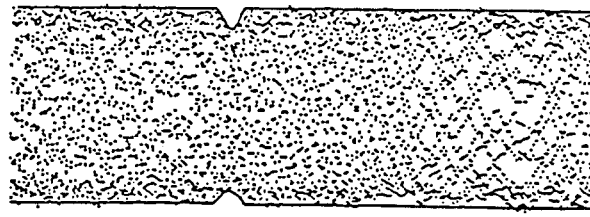
Carrier signal amplitude
Fig. 5

OPTICAL APPARATUS AND METHOD

This is a continuation of application Ser. No. 07/216,626, filed as PCT GB87/00752 on Oct. 23, 1987, published as WO88/03266 on May 5, 1988, which was abandoned upon the filing hereof.

This invention relates to apparatus for and methods of analysis of optically active materials. In particular, it relates to apparatus usable in high pressure liquid chromatography.

High pressure liquid chromatography is used in the pharmaceutical and food industries, inter alia, for the analysis of enantiomers of optically-active compounds. One application is to demonstrate the absence of a biologically less active enantiomer of an optically-active product. Existing detection systems do not possess this selectivity.

In U.S. Pat. No. 4,498,774 there is described a liquid chromatography detector using a gas laser as radiation source. This high power radiation source is employed to give a very high ultimate signal-to-noise ratio (S/N). To use this power to its full advantage, very high quality chosen prism pairs are needed to give a depolarisation ratio of around $10^{-10}$, and also an intensity stabilisation unit on the laser output to reduce the flicker noise contribution. To retain the low depolarisation ratio air based modulators are used, giving only a very small modulation angle.

Analysis shows the need for a powerful light source for good signal/noise ratios, with S/N improving as the square root of the light source power, P. Although the signal/noise ratio is generally a function of depolarisation ratio, $\Delta$ and modulation angle $\theta$, the ultimate signal/noise ratio attainable for a given laser power is independent of these parameters.

Our polarimeter uses a collimated laser diode radiation source at 820 nm which has an inherently low amplitude noise characteristic. This allows the use of a polariser/analyser with a depolarisation ratio of $10^{-5}$ to $10^{-6}$ and glass-based Faraday modulators as the extra depolarised light transmitted carries little amplitude noise. An external intensity stabilisation unit is not necessary.

Hitherto, diode laser radiation sources have not proved suitable for use in optical polarimeters due to highly divergent output which is unsuitable for focussing through a microbore sample cell. Furthermore, due to the dependence of the specific rotation of optically active materials on the inverse square of the wavelength of the analysing radiation, shorter wavelengths have been preferred. Commercially available polarimeters have used mercury lamp sources at 302 nm or 365 nm to take advantage of the higher specific rotation at those wavelengths.

We have found that use of a solid-state diode laser based optical-rotation detector permits an improvement in stability, and similar or potentially better short-term signal-to-noise ratio than a refractive-index detector. The optical rotation detector is also compatible with gradient elution, whereas refractive index is not. The detector is particularly useful with materials which lack accessible ultra-violet chromophores, for example sugars and polysaccharides.

According to the present invention there is provided apparatus for use in the analysis of optically-active materials comprising a solid state radiation source, container means for a sample of material under examination through which radiation from said radiation source passes to a detector, polariser means disposed between said radiation source and said container means, analyser means disposed between said detector and said container, together with modulation means disposed between said polariser and said container to modulate the rotation of the polarisation of radiation from said radiation source.

According to an alternative embodiment of the invention there is provided a polarimeter comprising a solid state source of radiation, fibre optic polariser means, modulator means to modulate radiation transmitted through said fibre optic polariser means, sample cell means for holding a sample under test, launch means for launching radiation from said polariser means into said sample cell, fibre optic analyser means, receiver means for receiving radiation from said sample cell means and detector means for detecting radiation transmitted by said fibre optic analyser means.

The invention will now be particularly described with reference to the accompanying drawings in which.

Figure 6A:
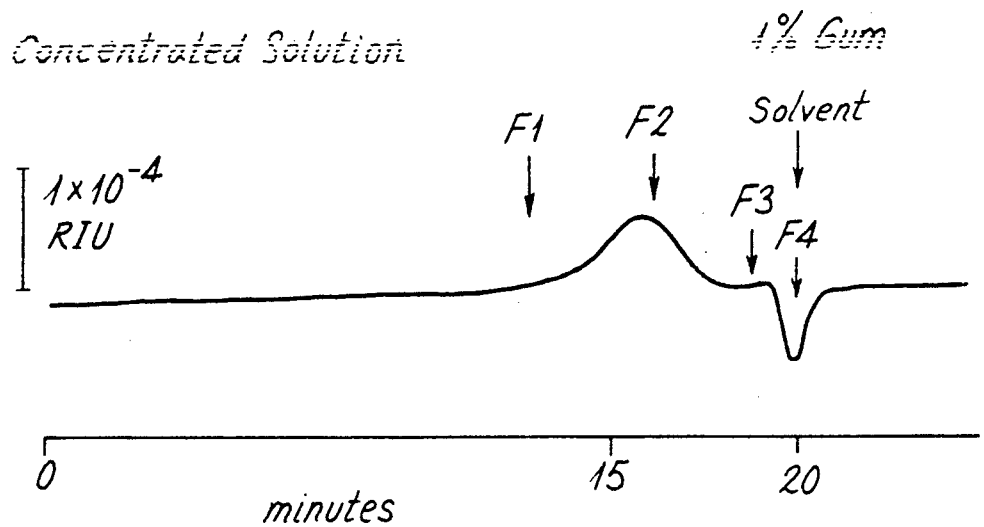
Figure 6B:
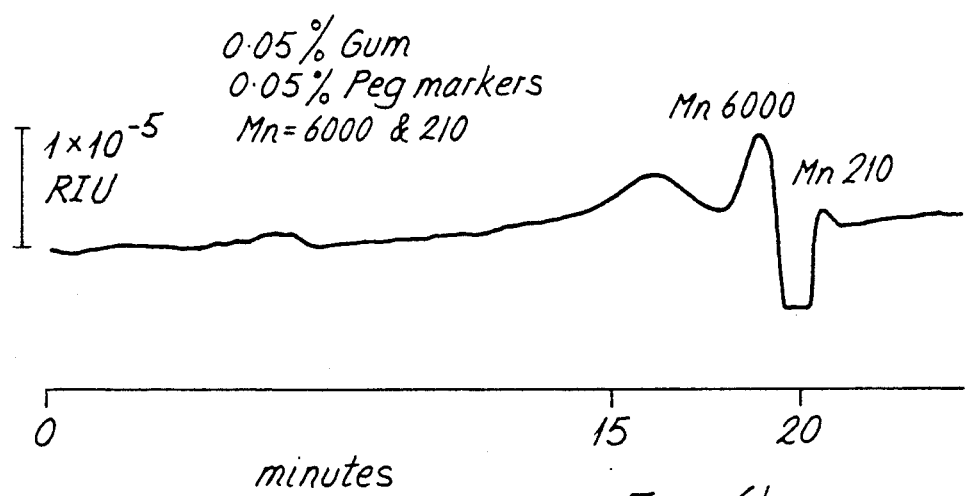
Figure 7:
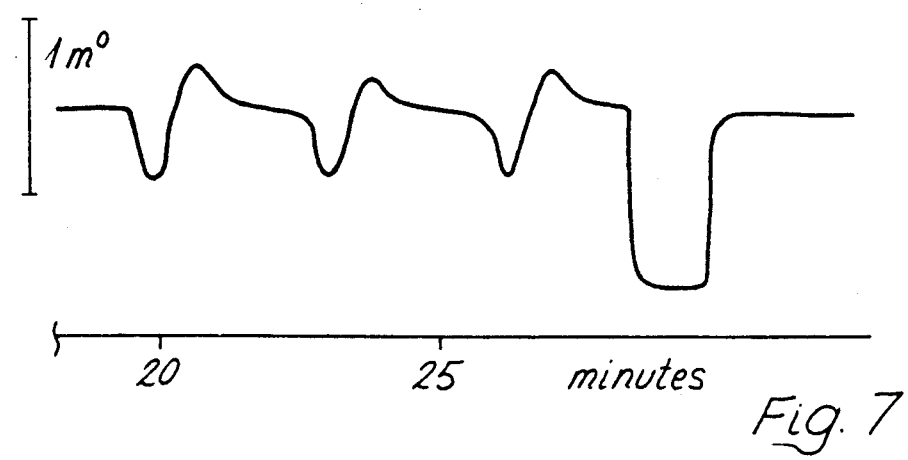
Figure 8:
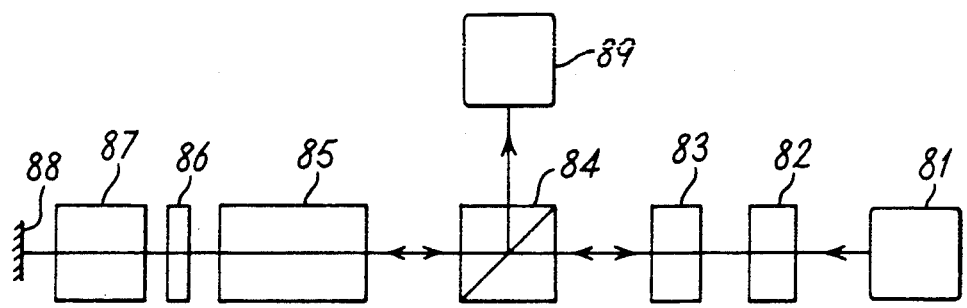
Figure 9:
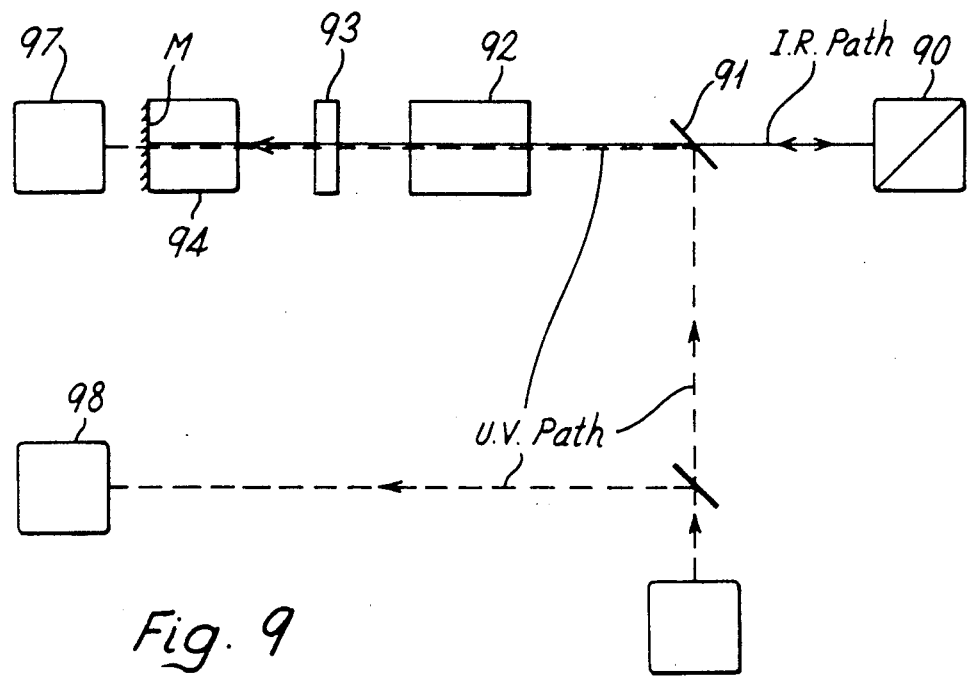
Figure 10:
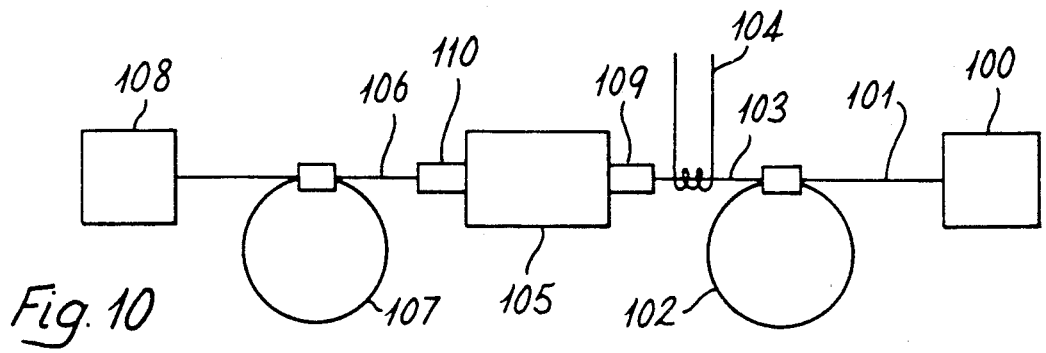
Figure 11:
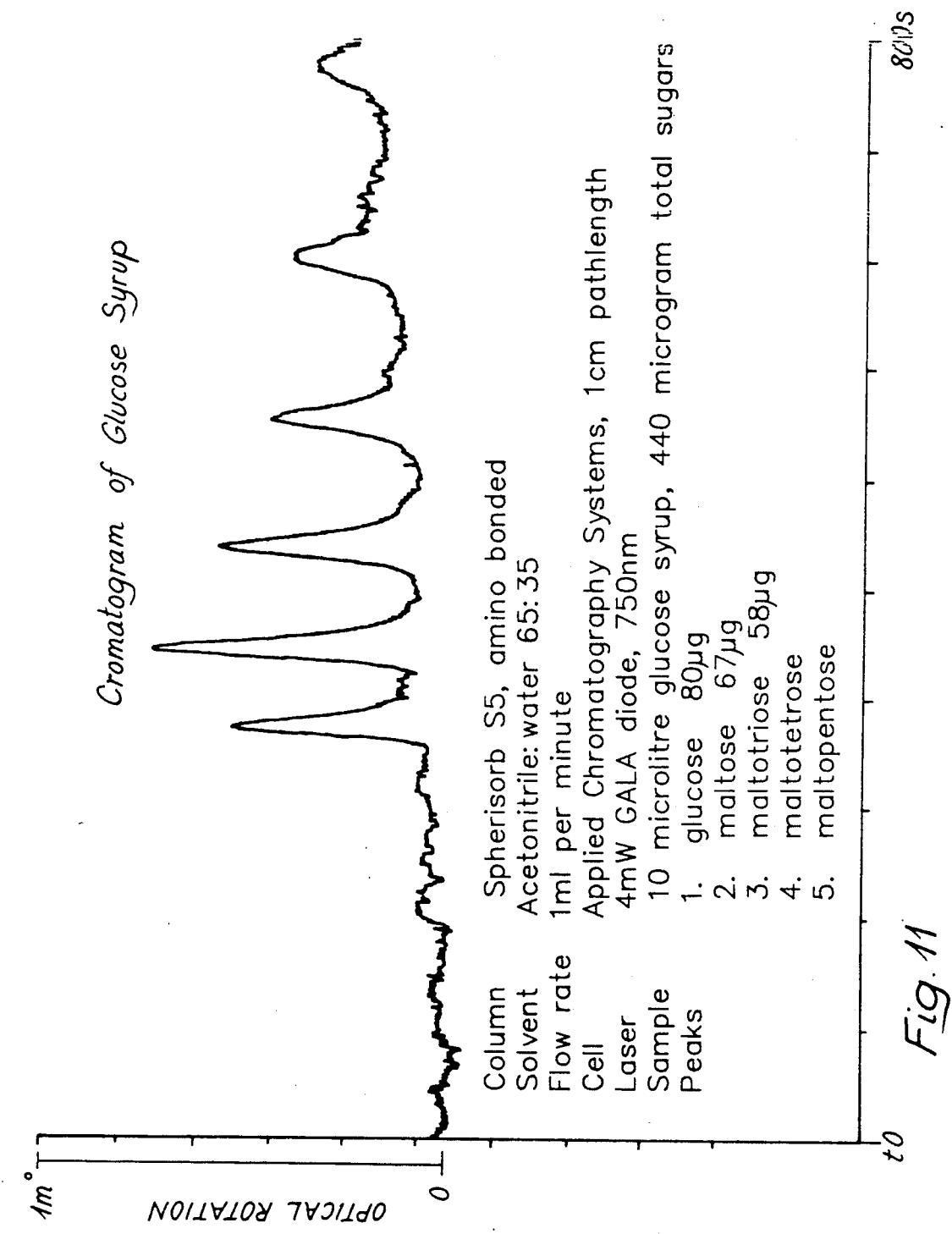

FIGS. 5a and b are chromatograms of gum acacia samples using optical rotation detection;

FIG. 5c is the carrier-signal amplitude during elution at a concentrated gum sample;

FIGS. 6a to b are chromatograms of gum acacia samples using refractive index detection;

FIG. 7 is a chromatogram showing reproducibility of results with the optical-rotation detection system;

FIGS. 8 to 10 show alternative embodiments of optical rotation detectors in accordance with the present invention;

FIG. 11 is a chromatogram of a sample of glucose syrup, and

Figure 12:
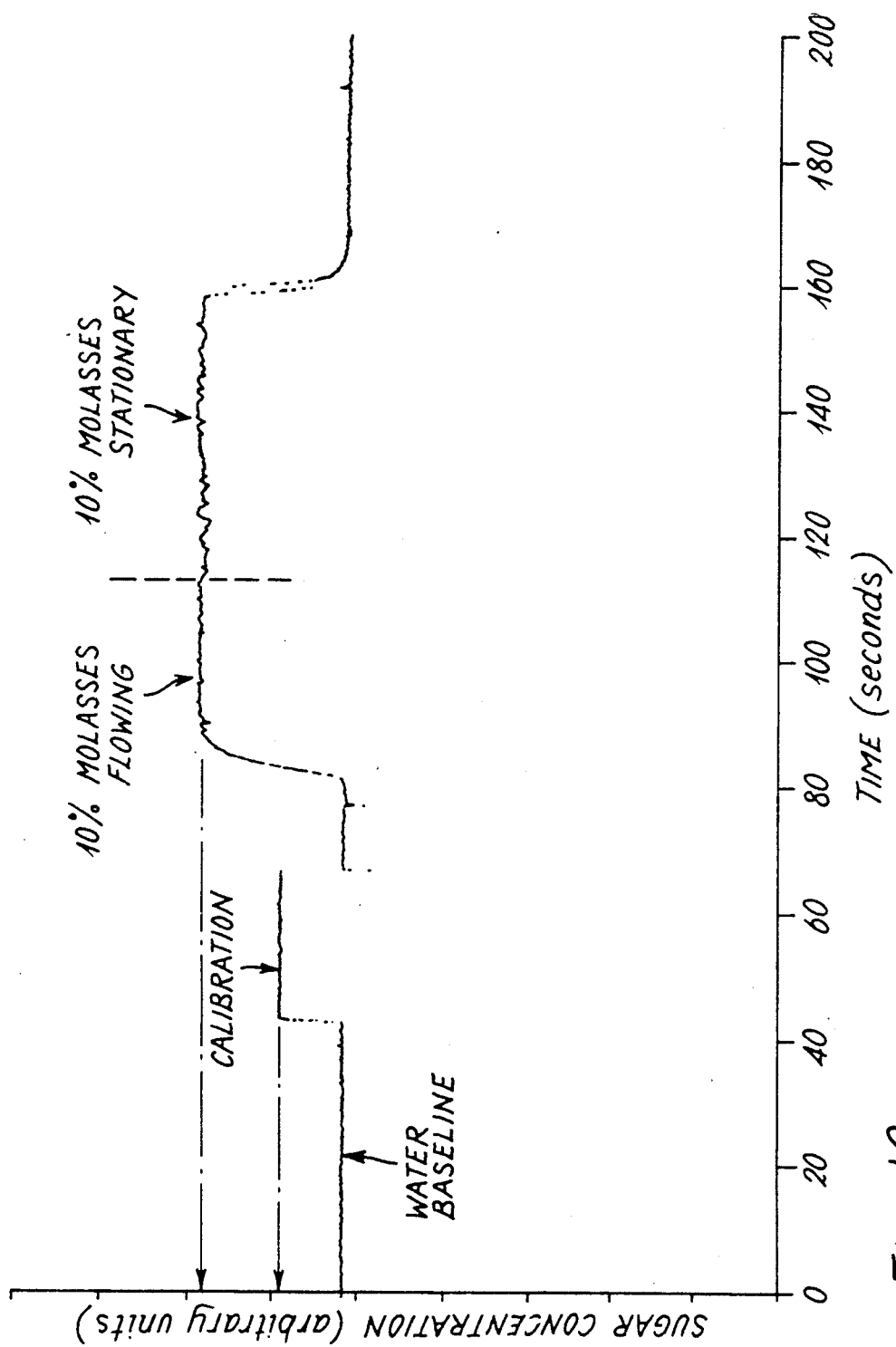

FIG. 12 shows rotation measurements made on a flowing molasses sample

Figure 1:
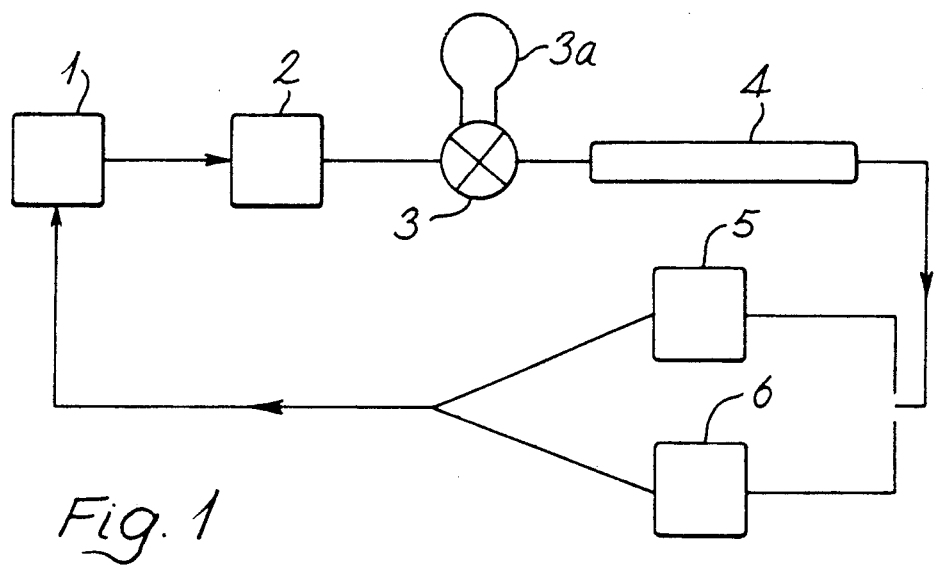
FIG. 1 is a schematic diagram of chromatographic apparatus in accordance with the invention.
Figure 2:
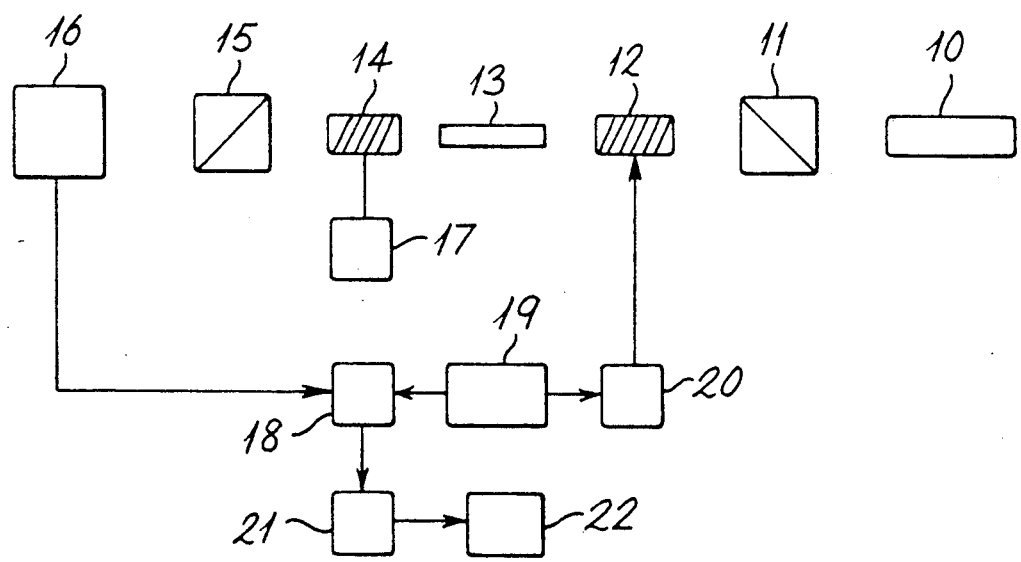
FIG. 2 is a block diagram of a laser optical rotation detector.
Figure 3:
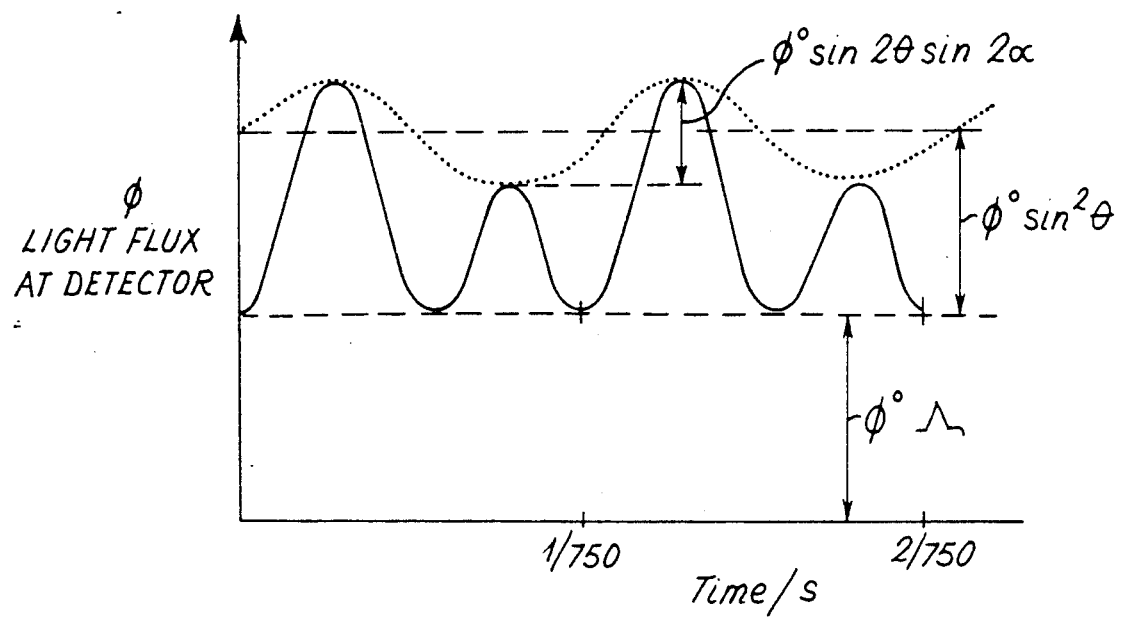
FIG. 3 is a diagram for purposes of explanation of the Faraday modulation technique.

Referring now to the drawings, FIG. 1 shows isocratic elution performed using a Constametric III HPLC pump 2 connected to a solvent reservoir 1 and a valve 3 with an injection loop 3A and chromatographic column 4. Detection was performed either by a laser optical-rotation detection 5, in accordance with the invention, or by a Refractometer III Model 1109 HPLC refractive index detector 6 for comparison purposes. The arrangement of the laser optical rotation detection is shown in FIG. 2. One milliwatt of 820 nm radiation from a collimated laser-diode source 10 passes through a polariser 11 and modulator 12 to a z-type cell 13 through which the HPLC eluent flows. Radiation from the cell passes by way of a calibrator 14 and analyser 15 to a detector 16. The calibrator is controlled by a DC power supply 17. The signal from the detector passes to a phase-sensitive detector 18 (Brookdeal 402) and then to a digital oscilloscope 21 and microcomputer 22 for data storage. A 750 Hz oscillator 19 drives a power oscillator 20 which controls the modulator, and provides a reference signal for the PSD. FIG. 3 illustrates the principle of operation. A 750 Hz signal applied to the Faraday modulator gives rise to a 750 Hz polarisation rotation of the light. When placed between polarisers crossed at exactly 90° this leads to a pure 1500 Hz carrier signal of varying amplitude and constant polarisation. Any variation from the polariser cross-point due either to misalignment or an optically active sample present in the cell gives rise to a 750 Hz amplitude modulation of the carrier signal. This is recovered by the amplifier/PSD combination. The amplitude of the carrier signal is also recorded and provides a measure of the time dependence of the light flux at the detector. With more concentrated solutions there may be a reduction in the carrier amplitude associated with the elution of intense peaks for certain designs. This is due to defocussing of the laser beam by lensing and Schlieren effects caused by mixing of solvent and sample fractions with mismatched densities within the sample cell. Unusual signals may occur at the output of the PSD during these defocussed periods.

Figure 4:
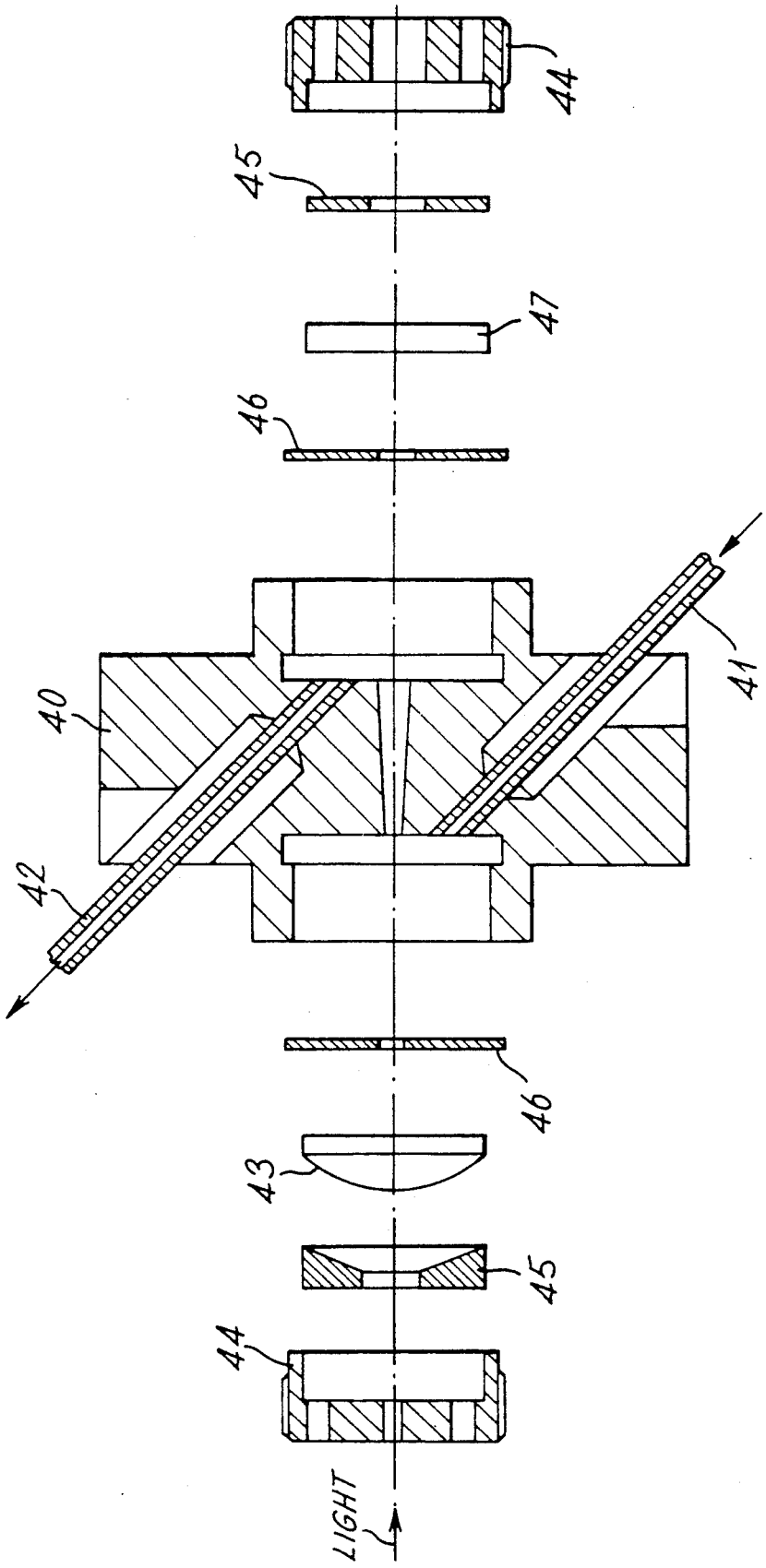
FIG. 4 is a section through a sample cell.

A sample cell free from defocussing effects is shown in FIG. 4. It comprises a cell body 40 having input and output tubes 41, 42 for the passage of the solution under test. Light enters the cell by way of plano-convex lens 43, which is held in place by means of a retainer 44, thrust washer 45 and gasket 46, and leaves by way of a window 47, which is similarly retained.

A reference may be provided by a photocell which receives exit radiation which has been rejected by the analyser. This gives an indication of total radiation throughput and may be used to correct the optical radiation signal for absorption effects.

The apparatus was tested in the analysis of gum acacia, a material which has a high polysaccharide content. Polysaccharides typically lack chromophores absorbing in the ultra-violet and visible region, thus cannot be analysed directly using a UV HPLC detector. Gum acacia is used industrially in confectionery products. Samples typically have the following composition.

| Constituent | Proportion | Molar mass |
| --- | --- | --- |
| 1. Protein rich | 4–15% | $10^6$ |
| 2. Polysaccharide rich | 70% | $10^5$ |
| 3. Possible autohydrolysis product | 20% | $10^4$ |

Separation is possible by size exclusion chromatography. Chromatograms were obtained of "instantised" (readily water-soluble) and native gum acacia. A TSK G5000 PW column provided optimum separation in the range $M_n \approx 10^5$. FIGS. 5 and 6 show a comparison of OR and RI detection using as mobile phase an aqueous, mildly alkaline buffer (1M $(NH_4)_2CO_3$). The protein rich fraction F1 appears as a shoulder to the RI and OR peaks of the principal fraction F2, which eluted in 16 minutes. The RI trace is positive, whilst the OR signal is negative. RI shows a further small positive peak at 19.1 minutes and an inverted peak at 20.0 minutes. OR reveals a large, sharp negative rotation fraction at 19.5 minutes and a broader positive rotation peak at 20.2 minutes. These we term fractions F3 and F4. FIG. 6 shows RI traces including polyethylene glycol markers with $M_n = 6000$ and 210. Fraction F3 elutes at a similar time to the $M_n = 6000$ marker, whilst fraction F4 elutes with the solvent and $M_n = 210$ marker.

The gum sample was diluted by a factor 10 for FIG. 5a, which shows fractions F3 and F4. With a 0.1 cm$^3$ injection the total loading was 50 μg. It can be seen the OR detector readily handles low concentration samples with less than 1 millidegree rotation. The R.M.S. noise level is 0.004 m°. Reproducibility is shown in FIG. 7, with 0.1 cm$^3$ samples injected every 3 minutes. Peak heights are $-339° \pm 7\mu°$ and $+193° \pm 10\mu°$. The baseline drift is negligible, whereas there was considerable drift on the RI detector of around $2 \times 10^{-6}$RIU on a $50 \times 10^{-6}$RIU scale. This is comparable to the amplitude of the main polysaccharide rich fraction for 0.02% gum solution. Despite good temperature control and operation over long time periods it was not possible to achieve the low drift figure of $2 \times 10^{-7}$RIU hr$^{-1}$ specified for this unit (Table 1). The OR detector would routinely attain a drift of $<4\mu°$hr$^{-1}$, comparable to short term noise, within a couple of hours of switch on. This time was greatly reduced using more modern PSDs (Brookdeal 9503 and 5207). The OR detector was not thermostatted. Peak areas were calculated to find the relative contributions of the fractions to the total optical rotation of the sample. The areas are in the ratio

| | Fraction | | |
| --- | --- | --- | --- |
| | F1 + F2 | F3 | F4 |
| Relative peak area | −2.5 | −1.4 | −1 |

Fraction 4 was not seen in RI, because it elutes with the solvent.

The performance data of the two detectors is summarised in Table 1.

TABLE 1

| | Comparison of refractive index and optical rotation detector performance | | | | |
| --- | --- | --- | --- | --- | --- |
| Detector | Cell volume | Noise[1] | Noise equivalent concentration/ g cm$^{-3}$ sucrose | Drift[2] | Drift equivalent in g cm$^{-3}$ sucrose |
| RID 3 | 10 ml | $4 \times 10^{-8}$ RIU | $3 \times 10^{-7}$ | $2 \times 10^{-7}$ RIU hr$^{-1}$ | $1.4 \times 10^{-6}$ |
| OR | 20 ml | $4 \times 10^{-6}$° | $5 \times 10^{-7}$ | $<4 \times 10^{-6}$°hour$^{-1}$ | $<5 \times 10^{-7}$ |

[1]RI noise measured with static water in the cell, 0.5s time constant (Manufacturer's specifications). OR noise measured in use, 3s time constant. A smaller figure is potentially attainable using a 20 mW collimated diode laser now manufactured by Mullard, in place of the 2 mW diode used in the present project.
[2]RI drift measured over one hour with thermostatted detector, ° 1° C. ambient temperature change maximum (Manufacturer's specifications). OR drift measured in operation with no temperature control.

FIG. 11 shows a separation of sugars from glucose syrup with isocratic elution on a Spherisorb S5 column. For this separation a collimated 750 nm 4 mW diode laser was used. The cell was an Applied Chromatography Systems 1 cm path length tapered cell. There were no defocussing effects with this cell.

The apparatus described above finds particular application with gradient elution, which cannot be handled by refractive index detectors due to solvent compositional fluctuations. One such application is the gradient elution of sugar polysaccharide mixtures. It may also be used for quality control of drugs. Only one enantiomer is generally pharmacologically active and optical rotation would give an immediate and absolute quantitation of the enantiometric purity. In this application the optical-rotation detector could be used in conjunction with an ultra-violet detector.

In an alternative embodiment (FIG. 8), radiation from a collimated laser diode 81 passes through an optical isolator consisting of a quarter-wave plate 82 and a polariser 83. It passes through a beam-splitter polariser/analyser 84 and is transmitted through a sample cell 85, quarter-wave plate 86 and Faraday modulator 87 to a mirror 88 at which it is reflected. The reflected beam returns through the modulator, quarter-wave plate and sample cell to the beam splitter, from which it is reflected to a photodiode detector 89.

In a further embodiment shown in FIG. 9, a combined ultra-violet absorption/optical rotation detector, radiation from an 820 nm wavelength radiation source (not shown) passes through a polariser/analyser 90 and a cold mirror 91 to a sample cell 92. It then passes through an 820 nm quarter-wave plate 93 and Faraday modulator 94. On the exit surface of the modulator is an 820 nm mirror which is transparent to ultra-violet radiation. The 820 nm beam is then reflected by this mirror through the sample cell again to the polariser/analyser and a detector (not shown). Ultra-violet radiation from a UV source 95 passes through a beam splitter 96 and is reflected by the cold mirror 91 through the sample cell to a photodiode/photomultiplier tube ultra-violet detector 97. A reference beam is reflected by the beam splitter to a monitor photodiode 98.

In a still further embodiment of the invention shown in FIG. 10. radiation from a diode laser 100 is directed using either a collimated diode/lens assembly or a fibre pigtail into a polarisation-preserving fibre 101 and a fibre polariser 102. The exit fibre 103 passes thorough a modulator 104, which may be either a Faraday effect modulator or a piezo-electric birefringence modulator. The radiation is then directed into a microsample cell 105. Exit radiation is transmitted by a further polarisation-preserving fibre 106 through a fibre polariser 107 to a photodiode detector 108. The entrance and exit fibres are coupled to the sample cell by means of Selfoc or similar graduated-index lenses 109,110.

Polarimeters operating in the visible or ultraviolet regions cannot readily be used to measure the optical rotation of the many materials which are strongly absorbing at these wavelengths. However, at 820 nm. very few materials are highly absorbing, allowing optical rotation measurements to be made using our polarimeter. Industrial application of this is in the online monitoring of dark sugar solutions and molasses in sugar refineries, permitting better process control. Current practice is to take samples and then dilute them until transmission is high enough in the visible region for measurement with an ordinary polarimeter. FIG. 12 shows rotation measurements made on a flowing molasses sample in a 0.5 mm pathlength cell with 1 mW laser power at 820 nm. For an online apparatus, a longer pathlength and more powerful laser may be preferable. The technique also finds application in other process monitoring involving chiral flow streams.

A detector in accordance with the invention could also be used as a high-quality laboratory polarimeter, with microdegree sensitivity offering orders of magnitude improvement in sensitivity over present commercially available equipment.

We claim:

1. Apparatus for use in the analysis of optically-active materials comprising:
   a radiation source, container means for a sample of material under examination through which radiation from said radiation source passes to a detector,
   polariser means disposed between said radiation source and said container means,
   analyser means disposed between said detector and said container, and
   modulation means disposed between said polariser and said container to modulate the rotation of the polarisation of radiation from said radiation source wherein:
   said radiation source is a solid state device, and
   said polariser means and said analyser means have a depolarisation ratio of the order of $10^{-5}$ to $10^{-6}$.

2. Apparatus for use in the analysis of optically-active materials as claimed in claim 1 characterised in that said radiation source is an infra-red radiation source.

3. Apparatus for use in the analysis of optically-active materials as claimed in claim 2 characterised in that said radiation source has a characteristic wavelength of the order of 800 nm.

4. Apparatus for use in the analysis of optically-active materials as claimed in claim 1 characterised in that said radiation source is a collimated laser diode.

5. Apparatus for use in the analysis of optically-active materials as claimed in claim 1 characterised in that said modulation means is adapted to cause polarisation rotation of the radiation from said radiation source.

6. Apparatus for use in the analysis of optically-active materials as claimed in claim 5 characterised in that said modulation means is adapted to cause polarisation rotation of the radiation from said radiation source at a frequency of the order of 750 Hz.

7. Apparatus for use in the analysis of optically-active materials as claimed in claim 1 characterised in that it includes means for measuring the absorption of said sample under test at ultra-violet wavelengths.

* * * * *